United States Patent [19]

Raghuprasad

[11] Patent Number: 5,634,472
[45] Date of Patent: Jun. 3, 1997

[54] PAIN MEASURMENT

[76] Inventor: Puthalath K. Raghuprasad, 6241 Riders Rd., Odessa, Tex. 79762

[21] Appl. No.: 385,949

[22] Filed: Feb. 9, 1995

[51] Int. Cl.$^6$ ........................................ A61B 5/00
[52] U.S. Cl. ........................ 128/742; 128/744; 606/20
[58] Field of Search ................................ 128/742, 744; 606/20, 22, 23, 25, 26

[56] References Cited

U.S. PATENT DOCUMENTS

| | | | |
|---|---|---|---|
| 2,453,841 | 11/1948 | Gluzek | 128/2 |
| 3,207,159 | 9/1965 | Tateisi | 128/303.1 |
| 3,274,995 | 9/1966 | Eidus | 128/2 |
| 3,533,397 | 10/1970 | Scher | 128/303 |
| 4,308,013 | 12/1981 | Major | 433/32 |
| 4,646,735 | 3/1987 | Seney | 128/303.1 |
| 4,763,666 | 8/1988 | Strian et al. | 128/742 |
| 4,844,091 | 7/1989 | Bellak | 128/744 |
| 4,886,063 | 12/1989 | Crews | 128/403 |
| 5,007,433 | 4/1991 | Hermsdorffer et al. | 128/742 |
| 5,012,817 | 5/1991 | Zeilinski et al. | 128/744 |
| 5,022,407 | 6/1991 | Horch et al. | 128/739 |
| 5,314,423 | 5/1994 | Seney | 606/20 |

OTHER PUBLICATIONS

European Patent Applications No. 0 428 125 A1 Published May 22, 1991.

*Primary Examiner*—Max Hindenberg
*Attorney, Agent, or Firm*—Marcus L. Bates

[57] ABSTRACT

A determination is quantitatively made of the severity of pain exhibited at a specified area on an animal by determining the magnitude of cooling required at the area of pain in order for the pain to be masked or made to disappear. The amount of cooling required for pain disappearance is considered directly related to the severity of the pain. Hence, by measuring the temperature depression required to mask the pain in a patient, an examiner can determine just how serious is the pain, and additionally provide guidance in the selection of a specific medicine. There is always some finite temperature depression required for true pain to disappear. Should the patient alleges that no pain relief is encountered by the cooling of the painful area, the examiner considers that the patient is faking his pain.

17 Claims, 1 Drawing Sheet

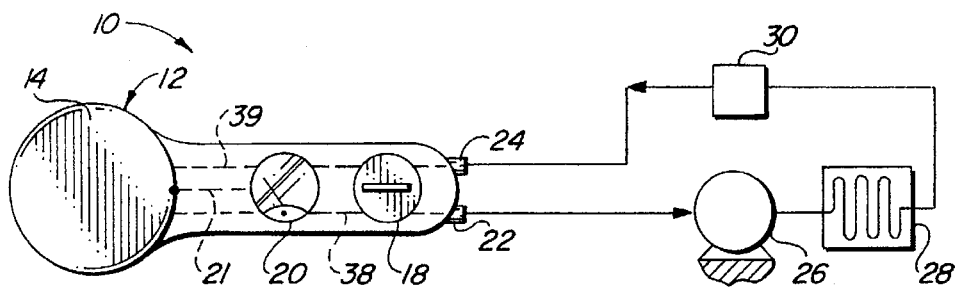
*FIG. 1*
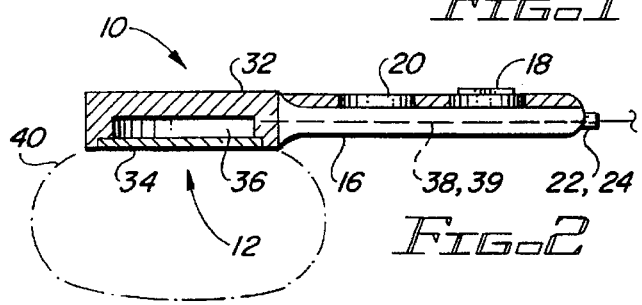
*FIG. 2*
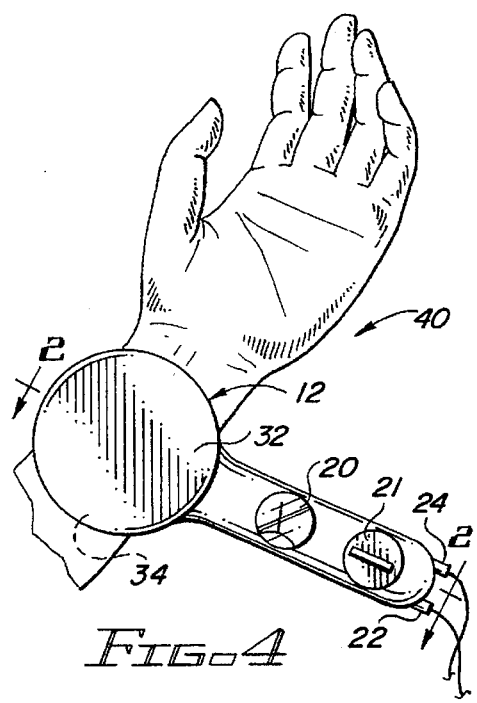
*FIG. 4*
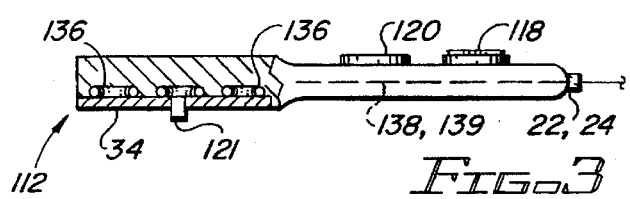
*FIG. 3*
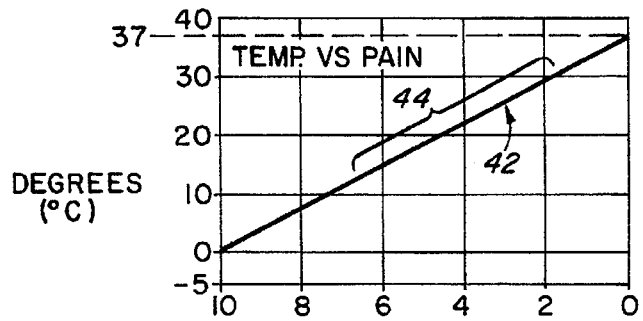
*FIG. 5*
*FIG. 6*
| PAIN SEVERITY (DOLS) | DRUG |
|---|---|
| 1–3 | ANALGESICS |
| 4–5 | NSAIDS |
| 6–8 | MILDER NARCOTICS AND/OR TRANQUILIZERS |
| >9 | STRONG NARCOTICS AND/OR OTHER MEASURES |

PAIN MEASURMENT

BACKGROUND OF THE INVENTION

The treatment of pain in a completely objective way has been hampered by the lack of means to measure pain. Usually when a patient complains of pain, physicians attempt to determine the nature of pain by asking the patient to first describe the pain (that is, sharp, dull, aching, piercing, burning etc.). Then an attempt is made to determine the severity by asking the patient if it was severe, moderate or mild. Some of the other characteristics, such as accompanying symptoms like sweating, palpitations (fast or irregular heart beats) fainting sensation etc or radiation from the focus of pain to a distant area or aggravation of pain by deep breathing, movements of body parts and relief obtained by various maneuvers, such as rubbing, local application of pressure, heat or cold are determined. With this data, in the context of all the other features of the illness, a determination is made as to the most appropriate treatment, including the type of pain relief medications. Such treatment is at best empiric and can not only fail but occasionally lead to many unwanted side effects. In some patients who complain of unusual pain or who feigns pain the whole treatment may fail or at least delay relief by many days or weeks. If one considers chronically painful conditions such as arthritis, back pain, headache, migraine or abdominal pain from various causes, one has to come up with appropriate adjustment in both the doses and, periodically, change in medications. Thus, some form of objective evaluation of pain is sorely required.

Some scientists have attempted to measure pain by various means. Most of such measures have included some form of inducing pain in another part of the body and asking the patient to grade their pain by comparison. This means of determining the severity of pain is impractical for repeated use and will be poorly tolerated by patients. If one considers the fact that the patient is already in pain, such measures to quantitate pain is downright barbaric. It is for this reason that an object of this invention is to achieve the same or better results by relieving pain rather than inducing more pain!

It is common experience that if cold temperature is applied to the part of the body that is painful, that is by applying ice cubes or ice cold water, most of the pain can be relieved quickly. How this is achieved is not completely understood but evidently the nerve endings and the pain sensing organs are "numbed" temporarily. The current invention makes use of this phenomenon to actually quantitate pain. It is anticipated that the reduction in temperature that is required to control pain will depend on the severity of pain, regardless of its cause.

Thus, an apparatus with a suitable probe that is cooled through a whole range of temperatures is required. If such a probe also measures the temperature of the part of the skin that is thus cooled, a system is in place for measuring pain.

The system will operate in the following manner: the operator selects a suitable tip or probe attached at the end of the apparatus and applies the probe over the area where the patient is experiencing pain. Then the temperature at the probe is gradually lowered after the patient is instructed to indicate immediately when pain relief is obtained. The instrument is then held at that temperature and skin surface temperature is measured. Either the change in temperature from room temperature or the actual skin surface temperature required to control pain is recorded and constitutes the degree of pain. One could easily assign a unit for this measurement. The term "DOL" is proposed for this unit (as "dolor" means pain in Latin). Some experimentation will then determine the degree of pain in various painful conditions in terms of "DOLs" and will serve as the standard against which patients will be assessed. Then one could take this information to its next logical step, that of determining the appropriate analgesic (pain relieving medication) or other means. Thus, guesswork is totally eliminated from the business of relieving pain. A useful by-product of this system of measuring pain is the categorization of the different types of pain into grades and in detecting when pain is not actually felt but imagined or faked.

Cryosurgical equipment (these are used to freeze lesions on skin or accessible other body parts for treatment) are in existence already and some of these already have all the ingredients of the sort of apparatus proposed. However, so far, they have only been used to remove diseased parts (e.g.: warts from skin or abnormal tissue from cervix of the uterus) and not for measuring pain. For this purpose the equipments may need gauges with graduations straddling the freezing point but none much below that value, unlike the usual cryosurgical equipments. It is envisioned that such pain measuring devices will become commonplace in headache/migraine clinics, rheumatologists' and orthopedic surgeons' offices, chiropractors' and dentists' offices and the like. Then one could confidently tell patients that their pain is of "this degree" and it needs "this group of medicine" for relief or its need for admission to hospital and/or i.v. narcotics etc.

BRIEF DESCRIPTION OF THE DRAWINGS

FIG. 1 is a part diagrammatical, part schematical, plan view of apparatus, including a cyroprobe, used in carrying out the method of the present invention;

FIG. 2 is a longitudinal, cross-sectional view taken along line 2—2 of the apparatus of FIG. 4;

FIG. 3 is a longitudinal, cross-sectional view of a modification of the apparatus of FIG. 2;

FIG. 4 is a partial plan view showing the apparatus of FIG. 1 in use on a person;

FIG. 5 discloses a curve showing a plot of data obtained in accordance with this invention; and, FIG. 6 sets forth a chart for use in carrying out part of the invention.

SUMMARY OF THE INVENTION

This invention discloses a method of determining the severity of pain exhibited at a specified area on a person or other animal by determining the magnitude of cooling required, hereinafter referred to as "depression in temperature", or $\Delta T$, at the area of pain until the pain disappears, hereinafter referred to as "pain threshold". The magnitude of the required cooling is proportional to the severity of the pain. Therefore, the seriousness of the pain may be determined by this analytical method, and additionally, the results obtained may be expressed in a quantitative expression to enable the proper selection of a specific medicine as well as the quantity or the dosage thereof. The expression is "DOLs" which has a range 0–10 with 1 being mild pain and 10 being severe pain.

Depression in temperature at the area of pain until the pain threshold is determined is achieved according to this invention by applying a heat transfer member or cyroprobe to the area of pain. There is connected to the heat transfer member a means for lowering the temperature thereof. The cooling process continues until a depressed temperature is reached where the pain becomes masked. The resultant depression in temperature (ΔT) is compared with previously stored data and the proper type and dosage of medicine that must be administrated to the patient is thereby ascertained.

Should the patient allege that no pain relief is encountered by adequate cooling of the painful area, the doctor can assume that the patient is faking his discomfort, or else the patient has imaginary (psychiatric) pain.

A primary object of the present invention is the provision of a method of determining the severity of pain exhibited at a specified area on a person or other animal by determining the magnitude of the depression in temperature required at the area of pain for the pain to disappear, thereby measuring the magnitude of the pain threshold.

Another object of the invention is to provide apparatus by which a cooled member is applied to a selected painful area of a person, to thereby depress the temperature of the area a measured amount that determines the pain threshold.

A further object of this invention is to disclose and provide method and apparatus by which the severity of the pain is determined, and how the results may be used to guide one in the selection of a specific medicine as well as the dosage thereof.

A still further object of this invention is to provide method and apparatus by which the magnitude of depression in temperature at the area of pain is measured to ascertain quantitatively the severity of pain, by applying a heat transfer member to the area of pain to depress the temperature until the pain is masked. The resultant data is compared with stored data to determine the appropriate medicine that must be administrated to the patient to properly treat his condition.

Another and still further object of this invention is the provision of method and apparatus by which a determination can be made respective to an area that is allegedly painful to enable a doctor to ascertain when the patient is faking his pain.

These and various other objects and advantages of the invention will become readily apparent to those skilled in the art upon reading the following detailed description and claims and by referring to the accompanying drawings.

The above objects are attained in accordance with the present invention by the provision of a method and a combination of elements for use in a manner substantially as described herein.

DETAILED DESCRIPTION OF THE PREFERRED EMBODIMENT

In FIG. 1, numeral 10 indicates apparatus assembled into a system made in accordance with the present invention for determining the severity of pain exhibited at a known area of a person's body. The system includes a heat exchanger device 12, also known as a cyroprobe, having a heat transfer member 14 for progressively cooling a known area of a person's body down to a predetermined temperature. The heat transfer member 14 is attached to a handle 16 thereof. Valve means 18 mounted on the handle controls the rate of coolant flowing to and from member 14, while temperature indicator 20 is connected by sensor means 21 in order to measure the temperature of member 14. Alternatively, a similar sensor device can be used to measure the skin temperature closely adjacent or underlying member 14.

Refrigerant flow lines are connected to the free end of the handle 16 at connections 22 and 24 to enable liquid and gaseous flow to occur to and from member 14. A gas compressor 26 is connected to a refrigerant condenser 28, which in turn is connected to an accumulator 30 within which liquid refrigerant is stored for providing flow of coolant to connection 24 of apparatus 12.

Throughout the figures of the drawings, like or similar numerals, wherever logical to do so, will indicate like or similar elements.

In FIG. 2, apparatus 12 has a main body 32 that supports a plate member 34 and forms an expansion or cooling chamber 36 therebetween. Therefore, chamber 36 is an evaporator for extracting heat from plate member 34 and thereby cooling member 34 to a predetermined lower temperature. Flow passageways 38 and 39 are connected to the before mentioned connectors 22 and 24, and convey coolant to and from the evaporator 36 and thereby cool plate member 34.

FIG. 3 sets forth an alternate embodiment of the heat exchanger device 12 of FIG. 1. In FIG. 3, there is a heat exchanger device 112 having valve device 118 and a temperature indicator 120. The flow connections 22, 24 are connected to the ends of a serpentine arranged metal tube 136. The tube 136 is attached in heat transfer relationship respective to the plate member 34. Accordingly, the face of the plate can be placed in contact with an area of the body that is in pain, and the refrigerant flowing at conduits 22, 24 will depress the temperature of the plate member 34 to thereby reduce the temperature at sensor device 121 which is adjacent to the painful area, as heat is transferred from the painful area of the person's body into the plate member 34, and then into the metal cooling tube 136.

In FIG. 4, numeral 40 indicates the limb of a person, but it could also be the limb of another animal. The outer face of the plate member 34 is placed in heat conducting relationship respective to the surface of the limb 40 and thereby exchanges heat therewith, which depresses the temperature thereof as the plate is progressively cooled below the limb temperature.

In FIG. 5, a curve 42 indicates the relationship of temperature depression of an area of a person's body versus pain severity, measured in DOLS. The curve 42 illustrates different skin temperature measurements showing the probable skin temperatures that may be encountered in order to provide pain relief (in DOLS) for different individuals. Numeral 44 generally indicates the usual range of threshold values, that is, the skin temperature (27 degrees centigrade down to 12 degrees centigrade) required for pain relief, ie: where pain disappears or is masked for the average patient.

The chart set forth in FIG. 6 is useful for determining the type of drug that can be prescribed for a patient and is based on the DOLS ascertained in FIG. 5. Other characteristics, including age, weight, physical condition, and other variables having a bearing on this subject matter, are ordinary factors well within the comprehension of the physician, and is also available from most larger pharmaceutical companies.

In FIG. 6, a mild pain evidenced by 1–3DOLS (obtained from FIG. 5) is treated with an analgesic, while a medium pain of 4–5 DOLS is treated with nonsteroidal anti-inflammatory medicine (NSAIDS), and a severe pain of 6–8 DOLS utilizes the milder narcotics with or without tranquillizers, depending upon the circumstances. A pain threshold of 9 DOLS and greater requires strong narcotics, sometime with other measures known to those skilled in the art.

EXAMPLE 1

A patient complains of a persistent pain at an area in the forearm. Consideration of the weight, age, overall health, and other pertinent attributes of the patient, herein referred to as the "characteristics" of the patient, is determined in accordance with well known procedures. Next the Physician must determine the severity of the pain, which heretofore has been difficult and unreliable because of the difference that people exhibit with respect to tolerance for pain.

Different people therefore have different tolerance to pain, and a severe pain to one person may be considered a mild pain to another. This is especially so with people who have a vivid imagination and cannot reasonably tolerate pain of any degree. Therefore, it is advantageous for an examiner to be able to make a quantitative determination of the person's pain by determining the cooling required (depression in temperature or $\Delta T$) at the immediate area of the pain to mask or cause the pain to disappear (pain threshold).

The amount of cooling (measured in degrees F. or degrees C.) to mask the pain (pain threshold) is directly related to the severity of the pain, regardless of one's sensitivity or description of his pain. Hence, by measuring the temperature depression required to mask the pain in a patient (pain threshold), along with judicious analysis, the examiner can determine just how serious the trouble may be, and additionally this data is valuable as a guide in aiding the selection of a specific medication as well as the dosage thereof.

This is achieved by applying a heat transfer device 12 to the area of pain as seen in FIG. 4. There should always be a lower temperature that relieves pain (make it stop hurting), whereupon the examiner can read the values at temperature indicator 20 and thereby make an appropriate selection of the proper medicine to prescribe for the patient, in accordance with the curve 42 seen in FIG. 5.

There is always some finite temperature depression required for true pain to disappear. If the patient alleges that no pain relief is encountered by the cooling of the painful area, the examiner knows that the patient is faking his pain, and that in reality no pain exists, or alternatively there are mental problems involved.

The temperature values of pain threshold for various different people is plotted and shown as a curve 42 on the hypothetical chart of FIG. 5. This stored data provides for measurements of pain severity in DOLS. For example, no relief of pain is achieved at body temperature, for that represents a zero temperature depression. A mild pain of 2.0 DOLS may require that the heat exchanger head 14 be adjusted to reduce the skin temperature from a body temperature of 37 degrees centigrade down to 27 degrees centigrade ($\Delta T=10$ degrees Centigrade). A moderate pain of 5 DOLS may require a larger temperature depression that achieves a skin temperature of 15 degrees C. ($\Delta T=37-15=22$ degrees C.). A severe pain may require still a greater skin temperature depression to lower the skin temperature to 5 degrees C. which is found to be 8 DOLS in the curve 42; while intense pain of 9–10 DOLS requires a temperature depression that results in a skin temperature near freezing and may be dangerous. Moreover, temperatures depressed to these extreme values is reason to suspect that the person may be faking the pain.

In FIG. 5, in accordance with this invention, the range of pain severity is assigned values 0–10 referred to herein as "DOLS". Hence a DOL is a quantitative measure of the pain that is experienced by the patient, and provides a means by which the selection as well as the quantity of medicine to be prescribed, the latter of which experienced professionals can estimate accurately.

After the severity of pain has been measured in DOLS, the specific medicine is selected from the chart of FIG. 6, and then the dosage of the selected medicine is determined by experience, or by referring to stored data related to the recommended dosage for the patients characteristics. This is accomplished by simple experimental work with a large number of people. From this data and the previous determination of the severity of pain, which includes determining if patient is faking, the optimum medicine as well as the recommended dosage for the patient is accurately determined.

I claim:

1. A method of determining the severity of pain at a selected area of a person's body according to the following steps:

step 1: preparing a dictionary of stored terms related to the magnitude of depression in temperature that is required at selected painful areas of a persons body in order to mask the pain and thereby apparently cause the pain to disappear;

step 2: progressively cooling a heat transfer member below said person's body temperature while contacting said selected area of said person's body with said heat transfer member and thereby progressively lower the temperature at said area of pain;

step 3: determining the magnitude of the depression in temperature that is required at said area of pain to mask the pain and apparently cause the pain to disappear;

step 4: comparing the results of step 3 to said dictionary of stored terms and thereby determine the severity of the pain.

2. The method of claim 1 and further including the following steps:

step 5: preparing a second dictionary of stored terms related to the selection of known medicines that are useful in alleviating pain as well as the dosage thereof according to a persons characteristics;

step 6: comparing the results of step 4 to said second dictionary of stored terms and thereby determine the selection of a specific medicine as well as the dosage thereof.

3. The method of claim 1 and further including the following steps:

step 5: providing stored data related to the selection and magnitude of dosage of a medicine that is indicated in order to treat persons of various physical characteristics;

step 6: integrating the data of steps 4 and 5.

4. The method of claim 1 and further including the steps of:

step 5: preparing another dictionary of stored terms related to the selection of a specific medicine according to pain severity and physical characteristics of a large number of people;

step 6: comparing the magnitude of step 4 to the data of step 5 for the selection of a specific medicine as well as the dosage thereof.

5. The method of claim 1 and further including the steps of:

carrying out step 2 by compressing a gas to provide a liquid refrigerant; expanding said liquid refrigerant into an expansion chamber that is connected in heat transfer relationship respective to said heat transfer member; connecting a temperature sensor apparatus to determine the temperature of said heat transfer member; and throttling the flow rate of said liquid refrigerant into said expansion chamber and thereby control the rate of heat transfer from said heat transfer member into said area of pain.

6. The method of claim 5 and further including the steps of:

determining the temperature depression achieved by said heat transfer member by attaching a temperature sensor to determine the temperature depression of said area of pain; and comparing the depression in temperature of said area with said stored data to determine selection and dosage of an appropriate medicine.

7. The method of claim 1 and further including the steps of:

providing stored data related to the magnitude of the required dosage of a specific medicine that is indicated in order to treat various magnitudes of severity of pain represented by various magnitudes of temperature differentials; and, considering that the severity of pain is negligible when the patient alleges that no pain relief is encountered by the cooling of the painful area.

8. The method of determining the severity of pain exhibited at a specified area in a human body according to the following steps:

step 1. determining the magnitude of temperature differential required to relieve pain by reducing the temperature at said specified area until the pain is masked;

step 2. determine from the first recited temperature differential the selection of the proper medicine to prescribe for the human body by comparing the results of step 1 with a dictionary of stored terms related to the magnitude of temperature depression and the dosage and selection of the proper medicine to prescribe for a large population of humans to provide statistically sound data;

step 3. determining the appropriate medicine by cooling the area of pain until the pain disappears;

step 4. providing stored data related to the magnitude of the required dosage of a specific medicine that is indicated in order to treat various magnitudes of severity of pain represented by various magnitudes of temperature differentials.

9. The method of claim 8 and further including the steps of:

upon the magnitude of the temperature differential approaching a statistical unreal value, due to the human faking his pain and alleging that no pain relief is encountered by the cooling of the painful area, the severity of pain is considered to be nil.

10. The method of claim 8 and further including the steps of:

carrying out step 1 by compressing a gas to provide a liquid refrigerant; expanding said liquid refrigerant into an expansion chamber that is connected in heat transfer relationship respective to a heat transfer member; connecting a temperature sensor apparatus to determine the temperature of said heat transfer member; and throttling the flow rate of said liquid refrigerant into said expansion chamber and thereby control the rate of heat transfer from said heat transfer member into said area of pain.

11. The method of claim 10 and further including the steps of:

determining the temperature depression achieved by said heat transfer member by attacking a temperature sensor to determined the temperature depression of said area of pain; and comprising the depression in temperature of said area with said stored data to determined selection and dosage of an appropriate medicine.

12. The method of claim 11 and further including the steps of:

carrying out step 3 by cooling the painful area until the skin temperature approaches zero degrees centigrade, and should no pain relief be encountered, assume that the human is faking his pain.

13. A method of determining the severity of pain exhibited at a specified area on a human body, according to the following steps:

A. selecting a large number of humans having various different degree of pain at various different specified areas;

B. accumulating data related to the magnitude of temperature depression required for the specified area on the humans in order for the pain to substantially disappear;

C. storing the accumulated data of step B to provide a dictionary of stored terms related to pain severity vs the magnitude of temperature depression at the specified area;

D. determining the magnitude of temperature differential required to relieve pain by reducing the temperature at said specified area on the human body until the pain is masked; and then selecting a medicine appropriate for treatment of said severity of pain exhibited at said specified area on said human body;

E. transferring the selected medicine to the human body, thereby determining the severity of pain and the appropriate medicine for optimum treatment of the area of pain in order that pain relief is achieved.

14. The method of claim 13 and further including the steps of:

carrying out step D by cooling the painful area until the skin temperature approaches zero degrees centigrade, and should no pain relief be encountered, assume that the human is faking his pain.

15. The method of claim 14 and further including the steps of:

cooling the area to a low temperature by applying a device having means to be cooled to the area of pain and depressing the temperature of the area in order to relieve pain and determining from the magnitude of the depressed temperature the selection of the proper medicine to prescribe for the human.

16. The method of claim 13 and further including the steps of:

considering that the severity of pain is negligible when the human alleges that no pain relief is encountered by the cooling of the painful area.

17. The method of claim 16 and further including the steps of:

carrying out step B by compressing a gas to provide a liquid refrigerant; expanding said liquid refrigerant into an expansion chamber that is connected in heat transfer relationship respective to said heat transfer member; connecting a temperature sensor apparatus to determine the temperature of said heat transfer member; and throttling the flow rate of said liquid refrigerant into said expansion chamber and thereby control the rate of heat transfer from said heat transfer member into said area of pain.

* * * * *